United States Patent
Senn-Bilfinger et al.

(10) Patent No.: US 6,653,477 B2
(45) Date of Patent: Nov. 25, 2003

(54) IMIDAZOPYRIDIN-8-ONES

(75) Inventors: Jörg Senn-Bilfinger, Constance (DE); Wilm Buhr, Constance (DE); Peter Zimmermann, Constance (DE)

(73) Assignee: Altana Pharma AG, Constance (DE)

( * ) Notice: Subject to any disclaimer, the term of this patent is extended or adjusted under 35 U.S.C. 154(b) by 10 days.

(21) Appl. No.: 10/182,652

(22) PCT Filed: Mar. 28, 2001

(86) PCT No.: PCT/EP01/03511
§ 371 (c)(1),
(2), (4) Date: Sep. 19, 2002

(87) PCT Pub. No.: WO01/72748
PCT Pub. Date: Oct. 4, 2001

(65) Prior Publication Data
US 2003/0153565 A1 Aug. 14, 2003

(51) Int. Cl.$^7$ ................................. C07D 47/04
(52) U.S. Cl. ........................ 546/121; 544/127
(58) Field of Search ............. 546/121; 544/127

(56) References Cited

FOREIGN PATENT DOCUMENTS

| WO | WO 98/42707 | * 10/1998 |
| WO | WO 98/54188 | 12/1998 |

OTHER PUBLICATIONS

Hafenbradl D et al. Angewandte Chemie, International Edition in English, (1996), 35(5), 545–7.*

* cited by examiner

*Primary Examiner*—Evelyn Mei Huang
(74) *Attorney, Agent, or Firm*—Nath & Associates PLLC; Gary M. Nath; Tood L. Juneau

(57) ABSTRACT

Compounds of formula (I), in which the substituents have the meanings mentioned in the description, are valuable intermediates for preparing active compounds for the prevention and treatment of gastrointestinal diseases.

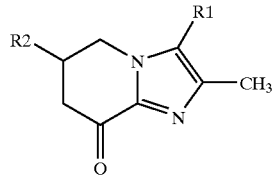

(1)

5 Claims, No Drawings

IMIDAZOPYRIDIN-8-ONES

FIELD OF APPLICATION OF THE INVENTION

The invention relates to novel compounds which are used in the pharmaceutical industry as intermediates for the production of medicaments.

1. Prior Art

The international patent applications WO98/42707 and WO 98/54188 disclose tricyclic imidazopyridine derivatives having a very specific substitution pattern, which should be suitable for the treatment of gastric and intestinal disorders.

2. Description of the Invention

The invention relates to compounds which can be used as important intermediates for the preparation of the compounds mentioned in the prior art and further compounds having a similar basic structure.

The invention thus relates in a first aspect to compounds of the formula 1

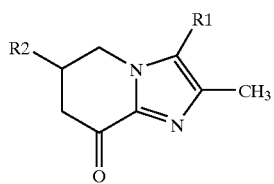

(1)

in which
R1 is hydrogen, methyl, formyl or hydroxymethyl and
R2 is hydrogen, halogen, carboxyl, —CO-1–4C-alkoxy, hydroxy-1–4C-alkyl, 1–4C-alkoxy-1–4C-1–4C-alkoxy-1–4C-alkoxy-1–4C-alkyl, fluoro-1–4C-alkoxy-1–4C-alkyl or the radical —CO—NR3R4, where
R3 is hydrogen, 1–7C-alkyl, hydroxy-1–4C-alkyl or 1–4C-alkoxy-1–4C-alkyl and
R4 is hydrogen, 1–7C-alkyl, hydroxy-1–4C-alkyl or 1–4C-alkoxy-1–4C-alkyl, or where
R3 and R4 together, including the nitrogen atom to which both are bonded, are a pyrrolidino, piperidine or morpholino radical,
and their salts.

Halogen within the meaning of the invention is bromine, chlorine or fluorine.

1–4C-Alkyl represents straight-chain or branched alkyl radicals having 1 to 4 carbon atoms. Examples which may be mentioned are the butyl radical, isobutyl radical, sec-butyl radical, tert-butyl radical, propyl radical, isopropyl radical, ethyl radical and the methyl radical.

1–4C-Alkoxy represents radicals which, in addition to the oxygen atom, contain a straight-chain branched alkyl radical having 1 to 4 carbon atoms. Examples which may be mentioned are the buto radical, isobutoxy radical, sec-butoxy radical, tert-butoxy radical, propoxy radical, isopropoxy radical and preferably the ethoxy radical and methoxy radical.

Hydroxy-1–4C-alkyl represents abovementioned 1–4C-alkyl radicals which are substituted by a hydro group. Examples which may be mentioned are the hydroxymethyl radical, the 2-hydroxyethyl radical and the 3-hydroxypropyl radical.

1–4C-Alkoxy-1–4C-alkyl represents one of the abovementioned 1–4C-alkyl radicals which is substituted by one of the abovementioned 1–4C-alkoxy radicals. Examples which may be mentioned are the methoxymethyl radical, the methoxyethyl radical and the butoxyethyl radical.

1–4C-Alkoxy-1–4C-alkoxy-1–4C-alkyl represents one of the abovementioned 1–4C-alkoxy-1–4C-alkyl radicals which is substituted by one of the abovementioned 1–4C-alkoxy radicals. An example which may be mentioned is the methoxyethoxymethyl radical.

Fluoro-1–4C-alkoxy-1–4C-alkyl represents one of the abovementioned 1–4C-alkyl radicals which is substituted by a fluoro-1–4C-alkoxy radical. Fluoro-1–4C-alkoxy in this case represents one of the above mentioned 1–4C-alkoxy radicals which is completely or partly substituted by fluorine. Examples of 1–4 alkoxy which is completely or partly substituted by fluorine, which may be mentioned, are the 1,1,1,3,3,3-hexafluoro-2-propoxy radical, the 2-trifluoromethyl-2-propoxy radical, the 1,1,1-trifluoropropoxy radical, the perfluoro-tert-butoxy radical, the 2,2,3,3,4,4,4-heptafluoro-1-butoxy radical, the 4,4,4-trifluoro-1-butoxy radical, the 2,2,3,3,3-pentafluoropropoxy radical, the perfluoroethoxy radical the 1,2,2-trifluoroethoxy radical, in particular the 1,1,2,2-tetrafluoroethoxy radical, the 2,2,2-trifluoryl ethoxy radical, the trifluoromethoxy radical and preferably the difluoromethoxy radical.

1–7C-Alkyl represents straight-chain or branched alkyl radicals having 1 to 7 carbon atoms. Examples which may be mentioned are the heptyl radical, isoheptyl radical (5-methylhexyl radical), hexyl radical, isohexyl radical (4-methylpentyl radical), neohexyl radical (3,3-dimethylbutyl radical), pentyl radical, isopentyl radical (3-methylbutyl radical), neopentyl radical (2,2-dimethylpropyl radical), butyl radical, isobutyl radical, sec-butyl radical, tert-butyl radical, propyl radical, isopropyl radical, ethyl radical and the methyl radical.

Suitable salts of compounds of the formula I are especially all acid addition salts. Particular mention may be made of the salts of the inorganic and organic acids customarily used. Those which are suit able are water-soluble and water-insoluble acid addition salts with acids such as hydrochloric acid hydrobromic acid, phosphoric acid, nitric acid, sulfuric acid, acetic acid, citric acid, D-gluconic acid benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid toluene-sulfonic acid, methanesulfonic acid or 3-hydroxy-2-naphthoic acid, where the acids are employed in salt preparation—depending on whether it is a mono- or polybasic acid and depending on which salt is desired—in an equimolar quantitative ratio or one differing therefrom.

It is known to the person skilled in the art that the compounds according to the invention and their salts if they are isolated, for example, in crystalline form, can contain various amounts of solvents. The invention therefore also comprises all solvates and in particular all hydrates of the compounds of the formula 1, and also all solvates and in particular all hydrates of the salts of the compounds of the formula 1.

Compounds of the formula 1 to be emphasized are those in which
R1 is methyl,
R2 is hydrogen, fluorine, chlorine, carboxyl, methoxycarbonyl, ethoxycarbonyl, hydroxymethyl, methoxyethoxymethyl, difluoromethoxymethyl or the radical —CO—NR3R4, where R3 is hydrogen, methyl, ethyl, propyl, 2-hydroxyethyl or 2-methoxyethyl and R4 is hydrogen, methyl or ethyl, and their salts.

Preferred compounds of the formula 1 are those in which

R1 is methyl,

R2 is hydrogen, fluorine, chlorine, methoxycarbonyl, ethoxycarbonyl, hydroxymethyl or methoxymethyl, and their salts.

The compounds according to the invention can be prepared, for example, according to the following reaction scheme.

Scheme

In the scheme below, the preparation of a compound 1 where R1 = CH$_3$ and R2 = —COOC$_2$H$_5$ is outlined by way of example.

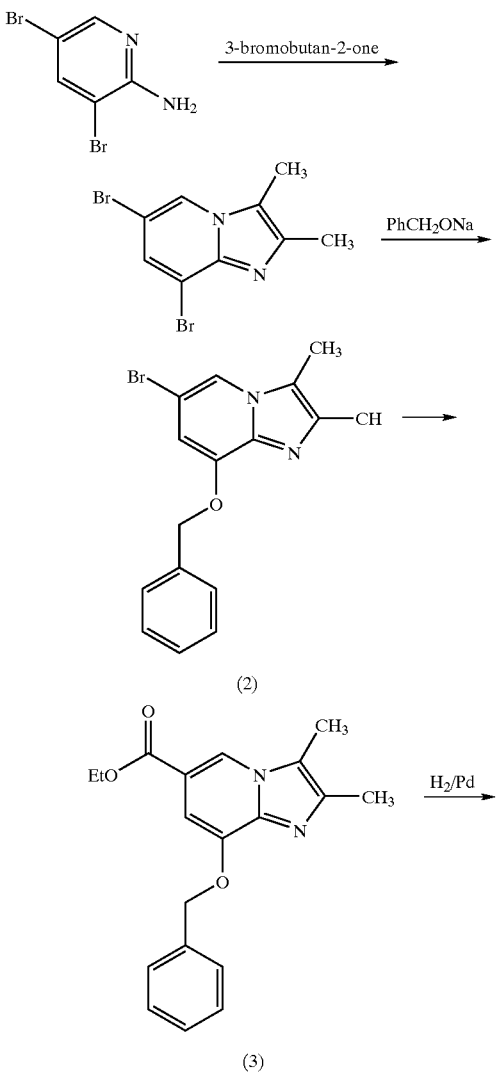

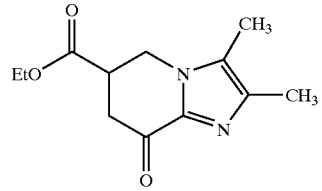

The reaction to give the compound 2 is carried out in a manner which is known per se to the person skilled in the art. The reaction of 2 to give 3 can be carried out in various ways, for example using the Heck reaction (with Pd(II), carbon monoxide and ethanol) or by metallation in the 6-position (with lithium or magnesium) and subsequent Grignard reaction. The metallation also offers the possibility of introducing other desired groups R2 in position 6, for example fluorine, chlorine or the carboxyl group The debenzylation/reduction of the compound 3 is likewise carried out in a manner known per se, for example using hydrogen/Pd(0). If compounds where R2=—CO—NR3R4 are desired, an appropriate derivatization can be carried out in a manner known per se (conversion of an ester into an amide) at the stage of compound 3 or after the debenzylation/reduction.

The following examples serve to illustrate the invention in greater detail without restricting it. Likewise further compounds of the formula 1 whose preparation is not described explicitly can be prepared in an analogous manner or in a manner familiar per se to the person skilled in the art using customary process techniques. The abbreviation min stands for minute(s) and h for hour(s).

EXAMPLES 1. 6,8-Dibromo-2,3-dimethylimidazo[1,2-a]pyridine

A mixture of 31.8 g of 2-amino-3,5-dibromopyridine, 22 g of 3-bromo-2-butanone and 350 ml of tetrahydrofuran is heated to reflux for 9 days, and the precipitate formed is filtered off and dried in vacuo is then suspended in 1 l of water and the suspension is adjusted to pH 8 using 6 molar aqueous sodium hydroxide solution. The precipitate formed here is filtered off and washed with water. 28 g of the title compound of melting point over 90° C. (sintering) are obtained.

2. 8-Benzyloxy-6-bromo-2,3-dimethylimidazo[1,2-a]pyridine 34.8 ml of benzyl alcohol are added dropwise with ice-cooling to a suspension of 13.5 g of sodium hydride (60% strength suspension in paraffin) in 510 ml of dimethylformamide and the mixture is stirred for 1 h until the evolution of gas is complete. 51.2 g of 6,8-dibromo-2,3-dimethylimidazo[1,2-a]pyridine are then introduced in small portions and the mixture is stirred at room temperature for 40 h. It is then poured onto 1 l of ice water, extracted three times with 100 ml of dichloromethane each time, the combined organic extracts are washed with saturated aqueous ammonium chloride solution and twice with water and concentrated to dryness in vacuo, and the residue is stirred with a little ethyl acetate. The precipitate obtained here is filtered off and dried in vacuo. 43.2 g of the title compound of melting point 151–3° C. (ethyl acetate) are obtained.

3. 8-Benzyloxy-6-ethoxycarbonyl-2,3-dimethylimidazo[1,2-a]pyridine

A mixture of 4 g of 8-benzyloxy-6-bromo-2,3-dimethylimidazo[1,2-a]pyridine, 0.4 g of palladium( acetate, 1.33 g of triphenylphosphine, 10 ml of triethylamine and 50 ml of ethanol is heated for 16 h) a carbon monoxide atmosphere in an autoclave (5 bar), the volatile portions are stripped off in vaco and the residue is chromatographed on silica gel (eluent: ethyl acetate). 2.4 g of the title compound melting point 140–1° C. (diethyl ether) are obtained.

4. 6-Ethoxycarbonyl-2,3-dimethyl-5,6,7,8-tetrahydrolmidazo[1,2-a]pyridine-8-one 3 g of 8-benzyloxy-6-ethoxycarbonyl-2,3-dimethylimidazo[1,2-a]pyridine, suspended in 50 ml of ethanol, are treated with 0.5 g of 10% strength palladium/active carbon and hydrogenated under a hydrogen pressure of 50 bar for 20 hours at an oil bath temperature of 75° C. After cooling, the catalyst is filtered off, the filtrate is concentrated to ⅕ of the volume in vacuo and the colorless precipitate formed here is filtered off. The filtrate from the precipitate is concentrated to dryness and chromatographed or silica gel (eluent: methylene chloride/methanol 100/3). 0.32 g of 6-ethoxycarbonyl-8-hydroxy-2,3-dimethyl-5,6,7,8-tetrahydroimidazo[1,2-a]pyridine is obtained. For conversion into the title compound, it is dissolved in chloroform, treated with 1.6 g of manganese dioxide and stirred at room temperature for 20 h. It is then filtered off, the filtrate is concentrated to dryness in vacuo and the residue obtained is purified on silica gel (eluent: methylene chloride/methanol 13/1). 0.2 g of the title compound of melting point 138–40° C. (diethyl ether) is obtained.

5. 8-Benzyloxy-6-hydroxymethyl-2,3-dimethylimidazo[1,2-a]pyridine

A solution of 1.2 g of 8-benzyloxy-6-ethoxycarbonyl-2,3-dimethylimidazo[1,2-a]pyridine in 20 ml of tetrahydrofuran is treated in small portions with 0.2 g of lithium aluminum hydride at room temperature stirred for one hour and treated successively with 0.2 ml of water, 0.2 ml of 6 molar sodium hydroxy solution and 0.6 ml of water. It is then extracted twice with methylene chloride (50 ml each), the combined organic phases are concentrated to dryness in vacuo and the residue is purified on silica (eluent: methylene chloride/methanol 13/1). 0.4 g of the title compound of melting point 213–5° C. (acetone) is obtained.

6. 6-Hydroxymethyl-2,3-dimethyl-5,6,7,8-tetrahydroimidazo[1,2-a]pyridin-8-one Analogously to the process described in Example 4, the title compound is obtained starting from 8-benzyloxy-6-hydroxymethyl-2,3-dimethylimidazo[1,2-a]pyridine by debenzylation/hydrogenation with palladium/active carbon.

7. 2,3-Dimethyl-6,7-dihydro-5H-imidazo[1,2-a]pyridin-8-one a) 500 g (2.35 mol) of 8-amino-2,3-dimethylimidazo[1,2-a]pyridine (see EP-A-299470) and 150 g palladium on active carbon (10% Pd), suspended in 5.0 l of 6N hydrochloric acid, are stirred at 50° C. I 24 h under a hydrogen pressure of 10 bar. The catalyst is filtered off and the reaction mixture is concentrated to 2.0 l in vacuo. The solution obtained is extracted with dichloromethane. The aqueous phase is adjusted to pH 4.8–5.0 using concentrated ammonia solution and again extracted with dichloromethane. This procedure is repeated ten times. The combined organic phases are dried over sodium sulfate and concentrated. The crude product is crystallized from isopropanol. 334.1 g of the title compound are obtained in the form of pale brown crystals of melting point 178.5° C. (isopropanol).

Alternatively, the title compound can be prepared as follows: b) A mixture of 252 g of 8-benzyloxy-2,3-dimethylimdazo[1,2-a]pyridine, 84 g of sodium hydrogencarbonate and 27 g of palladium/carbon catalyst (100% strength) in 500 ml of methanol is initially hydrogenated at 40° C. with hydrogen (5 bar) in an autoclave (20 h). The temperature is then reduced 20° and the hydrogen pressure to 2 bar and hydrogenation is continued until the slow absorption of hydrogen is complete (about 10 h, TLC checking). The catalyst is then filtered off, the filter cake is washed with 200 ml of methanol, the filtrate is concentrated to dryness in vacuo, the residue is stirred with 200 ml of chloroform and insoluble material is filtered off. The filter cake is washed well with 150 ml of chloroform and the filtrate is concentrated to dryness in vacuo. 142 g of the title compound of melting point 178–9° C. (2-propanol) are obtained.

8. 2-Methyl-6,7-dihydro-5H-imidazo[1,2-a]pyridin-8-one

Analogously to the process described in Example 7a and starting from the compound 8-aminomethylimidazo[1,2-a]pyridine described in EP-A-299470, the title compound is obtained as a ligl brown solid of melting point 147–9° C. (dichloromethane).

9. 3-Formyl-2-methyl-6,7-dihydro-5H-imidazo[1,2-a]pyridin-8-one

Analogously to the process described in Example 7a, the title compound is obtained starting from compound 8-amino-3-formyl-2-methylimidazo[1,2-a]pyridine described in EP-A-299470.

10. 6-Chloro-2-methyl-6,7-dihydro-5H-imidazo[1,2-a]pyridin-8-one

Analogously to the process described in Example 4, the title compound is obtained starting from 8-benzyloxy-6-chloro-2-methylimidazo[1,2-a]pyridine (EP-A-299470) by debenzylation/hydrogenation with palladium/active carbon.

11. 6-Chloro-3-formyl-2-methyl-6,7-dihydro-5H-imidazo[1,2-a]pyridin-8-one

Analogously to the process described in Example 4, the title compound is obtained starting from 8-benzyloxy-6-chloro-3-formyl-2-methylimidazo[1,2-a]pyridine (EP-A-299470) by debenzylation/hydrogenation with palladium/active carbon.

12. 6-Methoxymethyl-2,3-dimethyl-6,7-dihydro-5H-imidazo[1,2-a]pyridin-8-one

Analogously to the process described in Example 4, the title compound of melting point 103–104° C. is obtained starting from 8-benzyloxy-6-methoxymethyl-2,3-dimethylimidazo[1,2-a]pyridine by debenzylation/hydrogenation with palladium/active carbon.

What is claimed is:

1. A compound of the formula 1

(1)

in which

R1 is hydrogen, methyl, formyl or hydroxymethyl and

R2 is hydrogen, halogen, carboxyl, —CO-1–4C-alkoxy, hydroxy-1–4C-alkyl, 1–4C-alkoxy-1–4C-alkyl, 1–4C-alkoxy-1–4C-alkoxy-1–4C-alkyl, fluoro-1–4C-alkoxy-1–4C-alkyl or the radical —CO—NR3R4, where R3 is hydrogen, 1–7C-alkyl, hydroxy-1–4C-alkyl or 1–4C-alkoxy-1–4C-alkyl and R4 is hydrogen, 1–7C-alkyl, hydroxy-1–4C-alkyl or 1–4C-alkoxy-1–4C-alkyl, or where R3 and R4 together, including the nitrogen atom to which both are bonded, are a pyrrolidino, piperidino or morpholino radical, or its salts.

2. A compound of the formula 1 as claimed in claim 1, in which

R1 is hydrogen, methyl or formyl and

R2 is hydrogen, halogen, carboxyl, —CO-1–4C-alkoxy, hydroxy-1–4C-alkyl, 1–4C-alkoxy-1–4C-alkoxy-1–4C-alkyl or fluoro-1–4C-alkoxy-1–4C-alkyl, or its salts.

3. A compound of the formula 1 as claimed in claim 1, in which

R1 is methyl and

R2 is hydrogen, halogen or —CO-1–4C-alkoxy, or its salts.

4. A compound of the formula 1 as claimed in claim 1, in which

R1 is methyl,

R2 is hydrogen, fluorine, chlorine, carboxyl, methoxycarbonyl, ethoxycarbonyl, hydroxymethyl, methoxyethoxymethyl, difluoromethoxymethyl or the radical —CO—NR3R4, where R3 is hydrogen, methyl, ethyl, propyl, 2-hydroxyethyl or 2-methoxyethyl and R4 is hydrogen, methyl or ethyl, or its salts.

5. A compound of the formula 1 as claimed in claim 1, in which

R1 is methyl,

R2 is hydrogen, fluorine, chlorine, methoxycarbonyl, ethoxycarbonyl, hydroxymethyl or methoxymethyl, or its salts.

* * * * *